(12) United States Patent
Wang et al.

(10) Patent No.: US 9,994,598 B1
(45) Date of Patent: Jun. 12, 2018

(54) POLYENE COMPOUND, PREPARATION METHOD AND USE THEREOF

(71) Applicant: CHEMVON BIOTECHNOLOGY CO., LTD., Shanghai (CN)

(72) Inventors: Meng Wang, Shanghai (CN); Qinghua Ye, Shanghai (CN); Fangdao Wang, Shanghai (CN); Maojun Cai, Shanghai (CN); Jie Zhou, Shanghai (CN); Dong Wang, Shanghai (CN)

(73) Assignee: CHEMVON BIOTECHNOLOGY CO., LTD., Shanghai (CN)

( * ) Notice: Subject to any disclaimer, the term of this patent is extended or adjusted under 35 U.S.C. 154(b) by 0 days. days.

(21) Appl. No.: 15/577,825

(22) PCT Filed: May 26, 2016

(86) PCT No.: PCT/CN2016/083427
§ 371 (c)(1),
(2) Date: Nov. 29, 2017

(87) PCT Pub. No.: WO2016/192564
PCT Pub. Date: Dec. 8, 2016

(30) Foreign Application Priority Data

May 29, 2015 (CN) .......................... 2015 1 0290561

(51) Int. Cl.
*C07F 7/18* (2006.01)
*C07C 401/00* (2006.01)
(52) U.S. Cl.
CPC .......... *C07F 7/1844* (2013.01); *C07C 401/00* (2013.01); *C07F 7/1892* (2013.01)
(58) Field of Classification Search
CPC ..... C07F 7/1844; C07F 7/1892; C07C 401/00
USPC ...................................................... 549/215
See application file for complete search history.

(56) References Cited

U.S. PATENT DOCUMENTS

| 6,184,398 B1 * | 2/2001 | Kawase ................ C07C 401/00 552/653 |
| 2004/0019023 A1 * | 1/2004 | Morikawa ............ A61K 31/592 514/167 |
| 2010/0217020 A1 * | 8/2010 | Ogasawara ............ C07C 33/44 549/540 |

FOREIGN PATENT DOCUMENTS

| CN | 1436170 A | 8/2003 |
| CN | 101316813 A | 12/2008 |
| EP | 1955999 A1 | 8/2008 |
| WO | 01/96293 A1 | 12/2001 |

OTHER PUBLICATIONS

Shimizu, K. et al, "Design and Evaluation of New Atipsoriatic Antedrug Candidates Having 16-en-22-oxa-vitamin D3 structures", Bioorganic & Medicinal Chemistry Letters, vol. 16, No. 12, Apr. 21, 2006, pp. 3323-3329.
J. Org. Chem., 1986, 3098-3108.
J. Org. Chem. 2001, 66, 626-629.
PCT International Search Report and Written Opinion dated Sep. 1, 2016 from corresponding Application No. PCT/CN2016/083427, 9 pages.

* cited by examiner

*Primary Examiner* — Daniel R Carcanague
(74) *Attorney, Agent, or Firm* — Dilworth IP LLC

(57) ABSTRACT

Disclosed are a polyene compound, preparation method and use thereof. Provided in the present invention is the preparation method of a polyene compound I, comprising the following steps: under an action of a base and in an organic solvent, conducting a Witting reaction on a compound II and a compound III to obtain the polyene compound I. By the preparation method in the present invention, a coupling reaction results in good product purity without producing an obvious by-product and involves no heavy metal, thus facilitating a control over product quality and costs, having a simple operation and mild reaction condition, enabling high reaction conversion, a high yield, few by-products, high resultant product purity, low production costs and simple post-processing, and being suitable for industrial production.

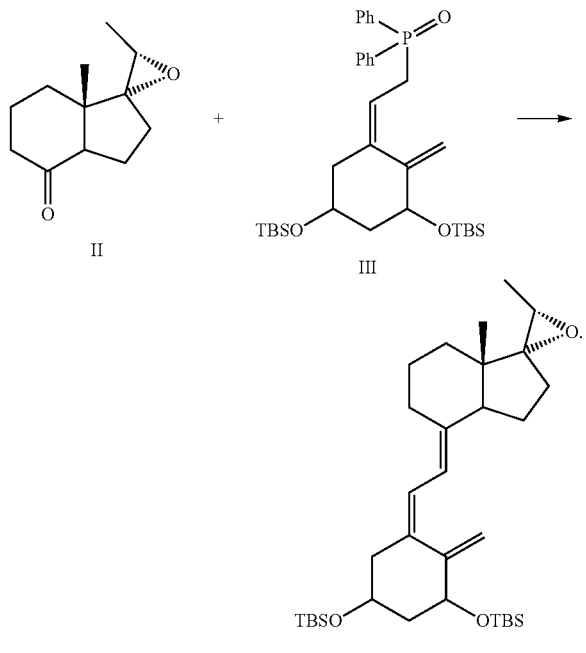

16 Claims, No Drawings

POLYENE COMPOUND, PREPARATION METHOD AND USE THEREOF

The present application claims the priority of Chinese Patent Application No. CN201510290561.4 filed on May 29, 2015, the contents of which are incorporated herein by reference in their entireties.

FIELD OF INVENTION

The present invention relates to a polyene compound, a preparation method and a use thereof.

BACKGROUND OF THE INVENTION

Vitamin D is a class of compounds with polyene structure, with important physiological activity. The common vitamin $D_3$ may be hydroxylated to 25-hydroxy vitamin $D_3$ [25-(OH)$D_3$] under the action of 25-hydroxylase in the liver cell mitochondria, and then be hydroxylated into 1,25-(OH)$_2D_3$ and 24,25-(OH)$_2D_3$ by the kidney. 1,25-(OH)$_2D_3$ or Calcitriol, a bioactive type of vitamin $D_3$, plays an important role in maintaining calcium and phosphorus metabolism balance and bone mineralization, and is used clinically for the treatment of renal osteodystrophy, parathyroid dysfunction, anti-vitamin D rickets and so on. During the clinical treatment of these lesions, the vitamin D analogues were have been found effective for the treatment of psoriasis, but easy to lead to hypercalcemia as side effect, which limits the application.

There are currently three types of vitamin $D_3$ analogues for the treatment of psoriasis: Calcitriol, Tacalcitol and Calcipotrol. No clear research results about their adverse effects on serum calcium have been found yet. So the development of new vitamin D compounds with better efficacy, less side effect of hypercalcemia and more clinical value in the treatment of psoriasis, will be a very meaningful work.

Pefcalcitol, a fluoroamide analogue, is a new compound developed by Chugai Corporation of Japan. Pefcalcitol has similar structure with Maxacalcitol and Calcitriol, with affinity for vitamin D receptors of 34%, 20% and 100%, respectively, but its in-vivo stability is 14 times than that of Maxacalcitol, and the antiproliferative activity is 12 times than that of Maxacalcitol and the calcium-related activity is only 17% of Maxacalcitol. These properties make Pefcalcitol a candidate compound for psoriasis with a higher selective therapeutic potential. The development of clean and efficient Pefcalcitol production process to meet the potential needs of clinical medication has significant economic and social effects.

In the prior art, the preparation of Pefcalcitol mainly has the following two routes:

(1) WO2001/96293 first reported the synthetic route of Pefcalcitol:

a basic molecular skeleton was constructed through a steroid, and then the ring thereof was opened under illumination to obtain the product, the specific synthetic route is as follows:

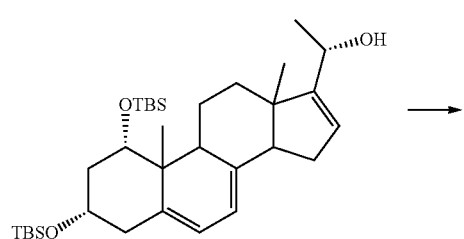

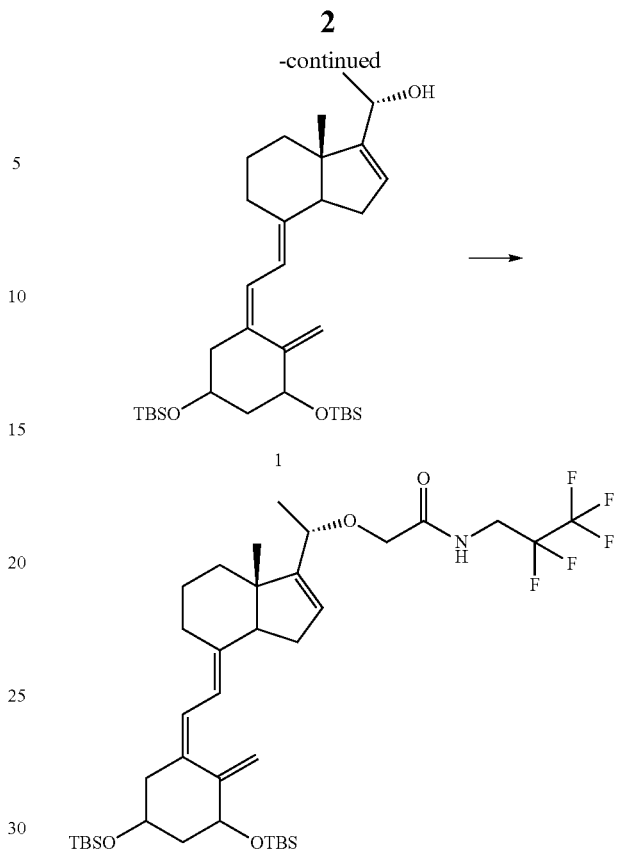

In the above method, the original inventor constructed a basic molecular skeleton through a steroid, and then the ring of which was opened under illumination to obtain the polyene compound 1, and finally obtained Pefcalcitol and the like. (See the literature Bioorganic & Medicinal Chemistry Letters 16 (2006) 3323-3329.).

The route is simple and short, but the yield of the key step of steroid ring-opening is very low, generally only 30-40%. This synthetic method uses the steroid reaction to construct a basic molecular skeleton first, but the steroid reaction needs to be fermented, as a result that the engineering control is difficult and the product quality is not high. Besides, the ring needs to be opened under illumination to obtain the product after obtaining the basic molecular skeleton in this synthesis method, but the illumination reaction requires the use of special reaction device, which has many control points, harsh process requirement, small reaction capacity and difficult impurity purification, and is not conducive to large-scale preparation of products.

In summary, the route is short, but has harsh requirements for the reaction device and conditions, which is difficult to achieve scale production; both the reaction conversion rate and the yield are low, and the cost is high; the steroid reaction and illumination ring-opening reaction are difficult to control, the purification of the impurity caused by illumination is difficult, making it difficult to achieve large-scale rapid preparation, therefore it is not appropriate to enlarge production.

(2) Chugai researchers in Japan applied for a patent route in 2006: EP1955999A1, the patent application designed a palladium-catalyzed total synthesis process, and reported that the target molecule was constructed through an allyl bromine intermediate and an enyne intermediate under the action of a palladium catalyst. This is an effective method for the total synthesis of vitamin D analogue. The specific synthetic route is as follows:

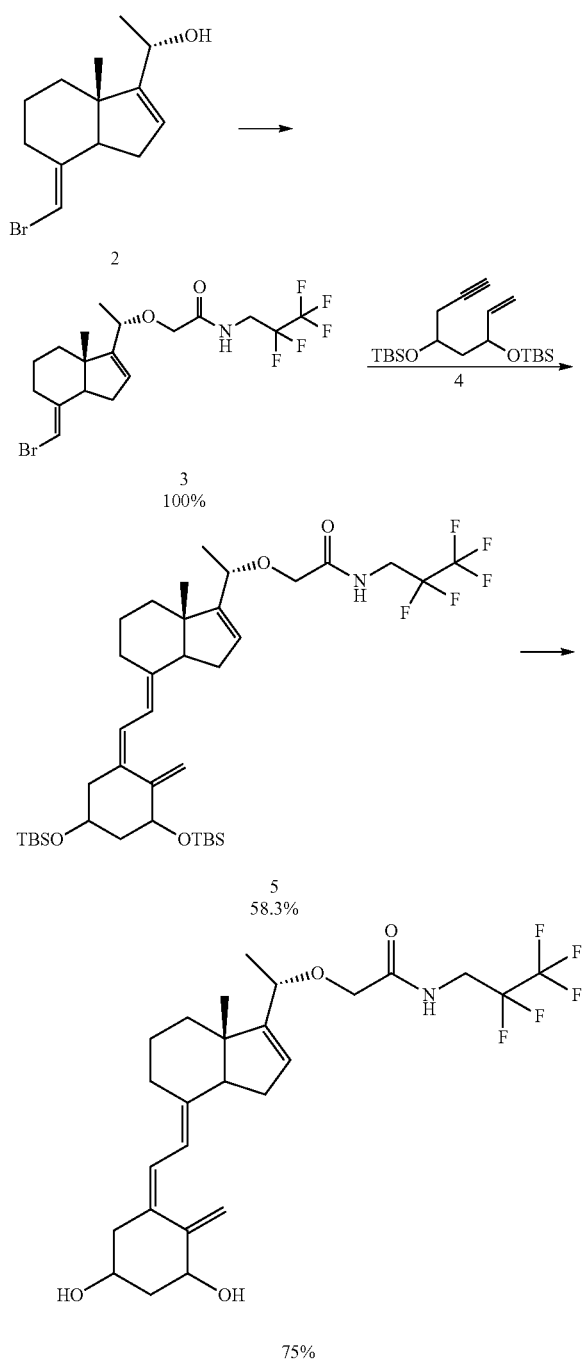

In the above method, the original inventor constructed the target molecule through an allyl bromide intermediate 3 and an enyne intermediate 4 under the action of a palladium catalyst, which is an effective method for the total synthesis of the vitamin D analogue. But the yield of the trost reaction itself is not high, only 58.3%, meanwhile the reaction conditions are harsh, special equipment is required, raw materials are more expensive, post-processing is cumbersome, the total yield of the route is only 43.7%. Therefore, it is not appropriate to enlarge production. In addition, catalyst involved reaction process is prone to produce elimination, rearrangement and other by-products; the use of precious metal catalyst palladium increases the cost, and affects the quality of the final product as well, the heavy metal residue limit needs to be strictly controlled in accordance with the requirements of ICH quality research, which will increase the difficulty of the process.

In summary, neither the route in which a basic molecular skeleton is constructed through the steroid first, and then the ring is opened under the illumination to obtain the product, nor the route in which the target molecule is constructed through an allyl bromine intermediate and an enyne intermediate under the action of a palladium catalyst, can obtain Pefcalcitol ideally. Accordingly, there is a strong need in the art for a new preparation method of Pefcalcitol to solve the above technical problems.

SUMMARY OF THE INVENTION

The technical problem to be solved in the present invention is for overcoming difficult key step, cumbersome steps, the use of precious metal catalysis, dangerous operation, serious environmental pollution, low yield, not suitable for industrial production and other defects existing in the preparation method of Pefcalcitol in the prior art, and provides a polyene compound, a preparation method and a use thereof.

In the preparation method of the present invention, the two key intermediates (compound II and compound III) may be prepared on a large scale, the use of convergent synthesis method is conducive to shorten the production cycle, and the quality of both fragments may be controlled. A coupling reaction results in good product purity without producing an obvious by-product and involves no heavy metal, thus facilitating a control over product quality and costs, having a simple operation and mild reaction condition, enabling high reaction conversion, a high yield, few by-products, high resultant product purity, low production costs and simple post-processing, and being suitable for industrial production.

The present invention provides a polyene compound I, comprising the following structure:

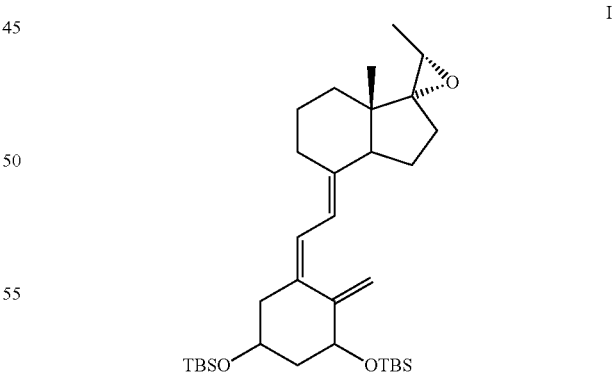

In the present invention, TBS represents tert-butyldimethylsilyl.

The present invention also provides a preparation method of the polyene compound I, comprising the following steps: under an action of a base and in an organic solvent, conducting a Wittig-Horner reaction on a compound II and a compound III to obtain the polyene compound I;

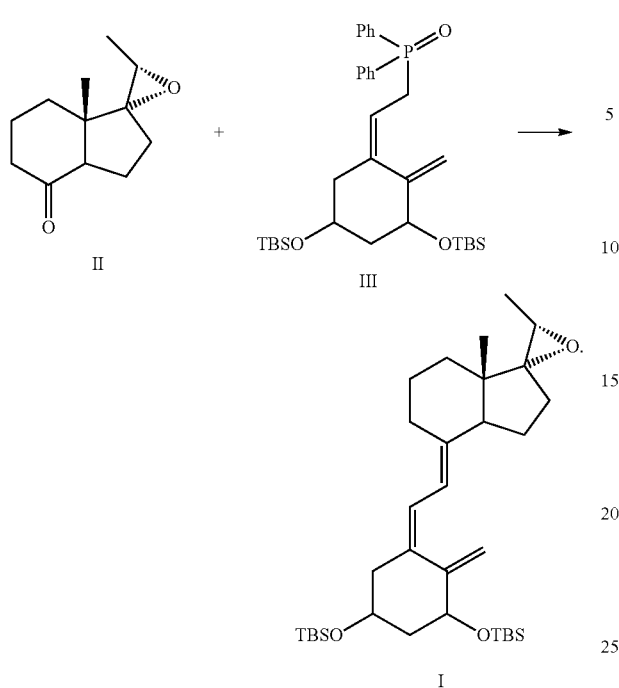

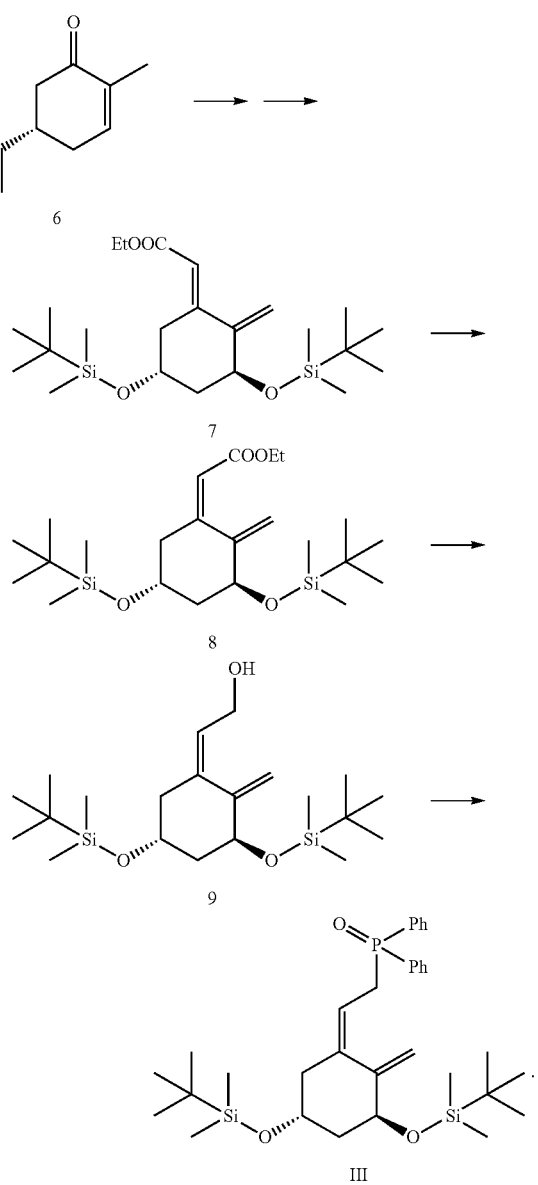

In the present invention, the preparation method of the polyene compound I may be a conventional method of Wittig-Horner reaction in the art, and the following reaction methods and conditions are particularly preferred in the present invention:

In the preparation method of the polyene compound I, the organic solvent is preferably an ether solvent, and the ether solvent is preferably one or more of tetrahydrofuran, methyltetrahydrofuran and methyl tert-butyl ether, and more preferably tetrahydrofuran.

In the preparation method of the polyene compound I, the volume-to-mass ratio of the organic solvent to the compound II is preferably 5 mL/g-50 mL/g, and more preferably 15 mL/g-50 mL/g.

In the preparation method of the polyene compound I, the base is preferably an organic base; the organic base is preferably one or more of butyllithium, lithium hexamethyldisilazide (LiHMDS), sodium hexamethyldisilazide (NaHMDS), potassiumhexamethyldisilazide (KHMDS) and lithium diisopropylamide, and more preferably one or more of lithium hexamethyldisilazide (LiHMDS), potassium hexamethyldisilazide (KHMDS) and sodium hexamethyldisilazide (NaHMDS).

In the preparation method of the polyene compound I, the molar ratio of the base to the compound II is preferably 0.8-1.5, and more preferably 0.9-1.3.

In the preparation method of the polyene compound I, the molar ratio of the compound III to the compound II is preferably 0.8-1.5, and more preferably 1-1.3.

In the preparation method of the polyene compound I, the temperature of the Wittig-Horner reaction is preferably −80° C. to −50° C. and more preferably −70° C. to −60° C.

In the preparation method of the polyene compound I, the progress of the Wittig-Horner reaction may be monitored using conventional monitoring methods in the art (e.g. TLC, HPLC or NMR), generally considering the disappearance of the compound II as the end of the reaction. The reaction time of the Wittig-Horner reaction is preferably 0.5 h-5.0 h, and more preferably 1.5 h-2.0 h.

In the preparation method of the polyene compound I, the compound III is prepared according to the method described in *J. Org. Chem.*, 1986, 3098-3108, using S-carvone 6 shown in the formula as the starting material to obtain the key intermediate 7 through multiple reactions, and then subjecting the intermediate 7 to cis-trans isomerism, reduction, chlorination and substitution reaction. The reaction formula is as follows:

The preparation method of the polyene compound I is preferably carried out in the presence of an inert gas, and when the preparation method of the polyene compound I is carried out in the presence of an inert gas, the inert gas is preferably one or more of nitrogen, helium, argon, neon, krypton and xenon, and more preferably nitrogen and/or argon.

The preparation method of the polyene compound I is preferably carried out under anhydrous conditions, and the anhydrous conditions may employ conventional operating conditions for anhydrous reaction in the art. The organic solvent is preferably an organic solvent after anhydrous treatment.

The preparation method of the polyene compound I preferably comprises step 1 or step 2, Step 1: Adding a base into a solution formed by the compound III and an organic solvent at the temperature of −60° C. to −70° C. under an inert gas, reacting for 10 min-30 min, then adding a mixture of the compound II and an organic solvent to carry out Wittig-Horner reaction to obtain the polyene compound I. The adding method is preferably dripping, with such a speed that the temperature of the reaction system is not more than −60° C. The organic solvent is preferably a conventional anhydrous organic solvent in the art.

Step 2: Adding a base into a solution formed by the compound II, the compound III and an organic solvent at the temperature of −60° C. to −70° C. under an inert gas to carry out Wittig-Horner reaction to obtain the polyene compound I. The adding method is preferably dripping, with such a speed that the temperature of the reaction system is not more than −60° C. The organic solvent is preferably a conventional anhydrous organic solvent in the art.

The preparation method of the polyene compound I preferably comprises the post-treatment steps of: after the completion of the reaction, quenching the reaction, extracting, washing, removing the organic solvent from the organic phase, and separating by column chromatography to obtain the purified polyene compound I. The reagent used in the quenching reaction is preferably saturated $NH_4Cl$ solution. The extraction may be carried out by a conventional method of operation in the art, and the solvent used for the extraction is preferably an ester solvent, and the ester solvent is preferably ethyl acetate. The separation by column chromatography may be carried out by the conventional method of operation in the art. The solvent used for column chromatography is preferably a mixed solvent of an ester solvent and an alkane solvent, the volume ratio of the ester solvent to the alkane solvent is preferably 1:5-1:20, further preferably 1:10-1:15. The ester solvent is preferably ethyl acetate, and the alkane solvent is preferably n-heptane and/or n-hexane.

The preparation method of the polyene compound I further comprises the steps of: reacting the compound VIII with an oxidizing agent in an organic solvent to obtain the compound II;

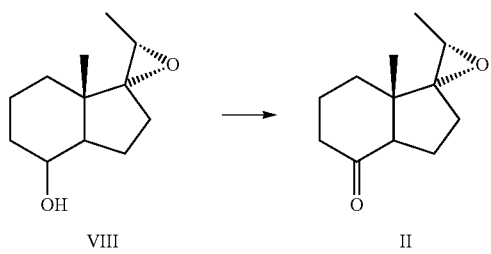

In the present invention, the preparation method of the compound II may be carried out by a conventional method of the oxidation reaction in the art, and the following reaction methods and conditions are particularly preferred in the present invention:

In the preparation method of the compound II, the organic solvent is preferably a halogenated hydrocarbon solvent; the halogenated hydrocarbon solvent is preferably a chlorinated hydrocarbon solvent; the chlorinated hydrocarbon solvent is preferably dichloromethane.

In the preparation method of the compound II, the volume-to-mass ratio of the organic solvent to the compound VIII is preferably 5 mL/g-20 mL/g, further preferably 7 mL/g-15 mL/g.

In the preparation method of the compound II, the oxidizing agent is preferably one of chromium trioxide-pyridine complex (PCC or sarret reagent), pyridinium dichromate (PDC), 1,1,1-triacetoxy-1,1-dihydro-1,2-benziodoxol-3-(1H)-one (Dess-Martin oxidant), sodium hypochlorite, or oxalyl chloride-dimethylsulfoxide oxidant (Swern oxidant).

In the preparation method of the compound II, the molar ratio of the oxidizing agent to compound VIII is preferably 1-5, more preferably 3-4.

In the preparation method of the compound II, when the oxidizing agent is an oxoyl chloride-dimethylsulfoxide oxidant (Swern oxidant), the oxidation reaction is preferably carried out in the presence of a base; the base is preferably an organic base, and the organic base is preferably triethylamine; the molar ratio of the base to the compound VIII is preferably 1-5, more preferably 3-5. The molar ratio of the dimethylsulfoxide to the oxalyl chloride is preferably 1-10, and more preferably 1-3. The molar ratio of the dimethylsulfoxide to the compound VIII is preferably 1-5, and more preferably 1-3.

In the preparation method of the compound II, the temperature of the oxidation reaction is preferably −80° C. to 50° C. When the oxidizing agent is an oxalyl chloride-dimethylsulfoxide oxidant (Swern oxidant), the temperature of the oxidation reaction is preferably −80° C. to −50° C., more preferably −70° C. to −60° C. When the oxidizing agent is one of chromium trioxide-pyridine complex (PCC or sarret reagent), pyridinium dichromate (PDC), and 1,1,1-triacetoxy-1,1-dihydro-1,2-benziodoxol-3-(1H)-one (Dess-Martin oxidant), the temperature of the oxidation reaction is preferably 0° C. to 50° C., more preferably 10° C. to 30° C.

In the preparation method of the compound II, the progress of the oxidation reaction may be monitored using conventional monitoring methods in the art (e.g., TLC, HPLC or NMR), generally considering the disappearance of compound VIII as the end of the reaction. The oxidation reaction time is preferably 0.5 h-5.0 h, and more preferably 1.5 h-2.0 h.

In the preparation method of the compound II, when the oxidizing agent is an oxoyl chloride-dimethylsulfoxide oxidant (Swern oxidant), the oxidation reaction is preferably carried out by the steps of: adding a solution formed by DMSO and an organic solvent into a solution formed by oxalyl chloride and an organic solvent at a temperature of −70° C. to −60° C. under an inert gas, reacting for 0.5 h-1 h; adding a solution formed by compound VIII and an organic solvent, reacting for 0.5 h-1 h; then adding a base to carry out an oxidation reaction to obtain the compound II. The adding method is preferably dripping, with such a speed that the temperature of the reaction system is not more than −60° C.

In the present invention, the preparation method of the compound II is preferably carried out in the presence of an inert gas, and when the preparation method of the compound II is carried out in the presence of an inert gas, the inert gas is preferably one or more of nitrogen, helium, argon, neon, krypton and xenon, and more preferably nitrogen and/or argon.

In the present invention, the preparation method of the compound II preferably comprises the post-treatment steps: after the completion of the reaction, quenching the reaction, extracting, washing and drying the reaction solution, and removing the solvent to obtain the compound II. The reagent used in the quenching reaction is preferably a saturated NH₄Cl solution. The extraction may be carried out in a conventional manner, wherein the solvent employed in the extraction is preferably one or more of a halogenated hydrocarbon solvent, an ether solvent and an ester solvent, the hydrocarbon solvent is preferably a chlorinated hydrocarbon solvent, and the chlorinated hydrocarbon solvent is preferably dichloromethane. The ester solvent is, for example, ethyl acetate. The ether solvent is, for example, methyl t-butyl ether.

In the present invention, the obtained compound II can be used after being purified by a conventional column chromatography method or used directly in the preparation of the compound I without further purification; preferably used directly in the preparation of the compound I without further purification.

The compound VIII mentioned in the preparation method of compound II may be prepared by the method described in the literature EP 1955999A1.

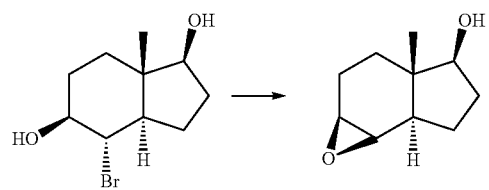

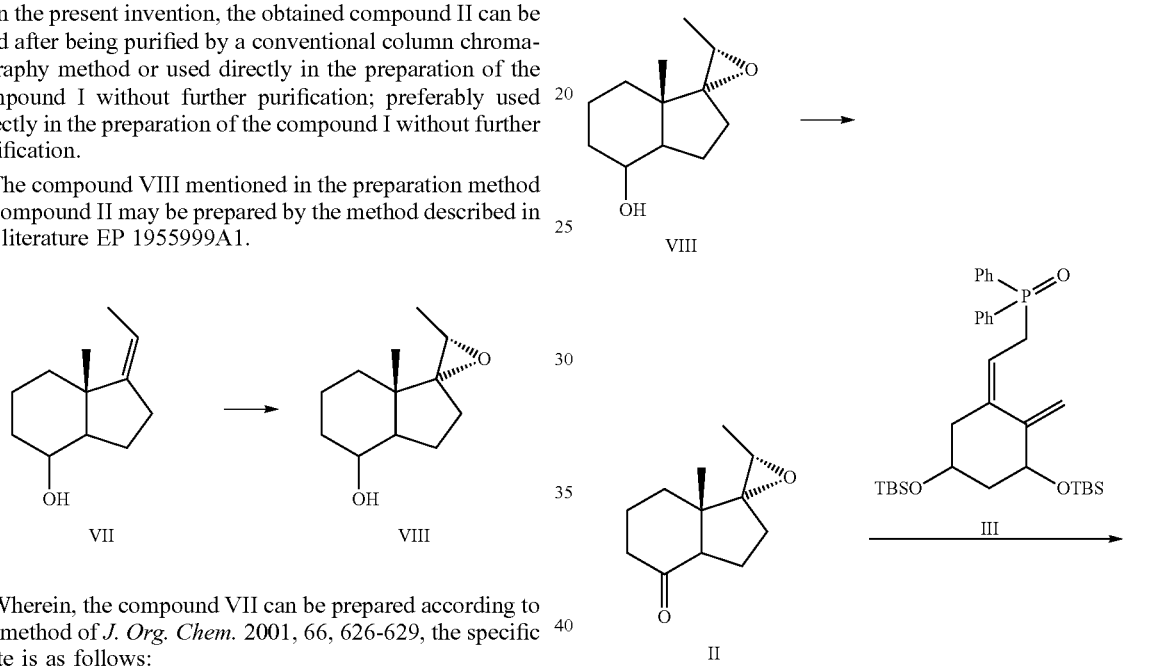

Wherein, the compound VII can be prepared according to the method of *J. Org. Chem.* 2001, 66, 626-629, the specific route is as follows:

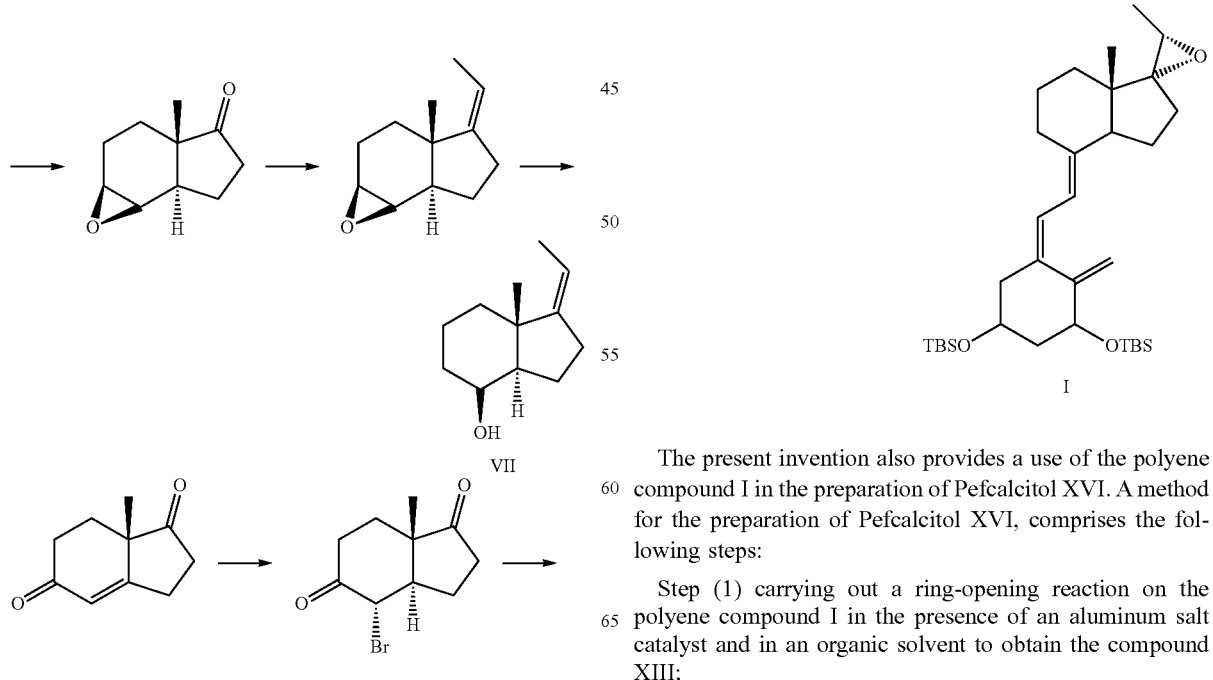

In the present invention, the preparation of the polyene compound I preferably comprises the following synthetic route:

The present invention also provides a use of the polyene compound I in the preparation of Pefcalcitol XVI. A method for the preparation of Pefcalcitol XVI, comprises the following steps:

Step (1) carrying out a ring-opening reaction on the polyene compound I in the presence of an aluminum salt catalyst and in an organic solvent to obtain the compound XIII;

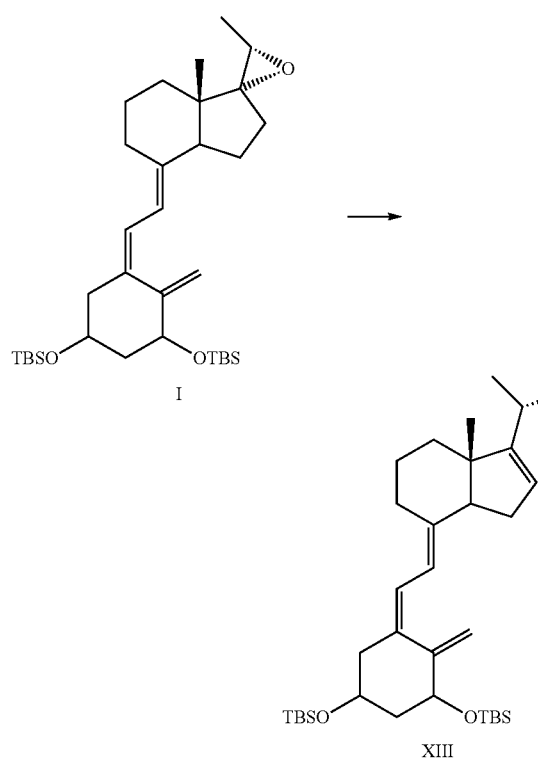

I

XIII

Step (2) carrying out a nucleophilic substitution reaction on the compound XIII with the compound XIV in the presence of a base in an organic solvent to obtain the compound XV;

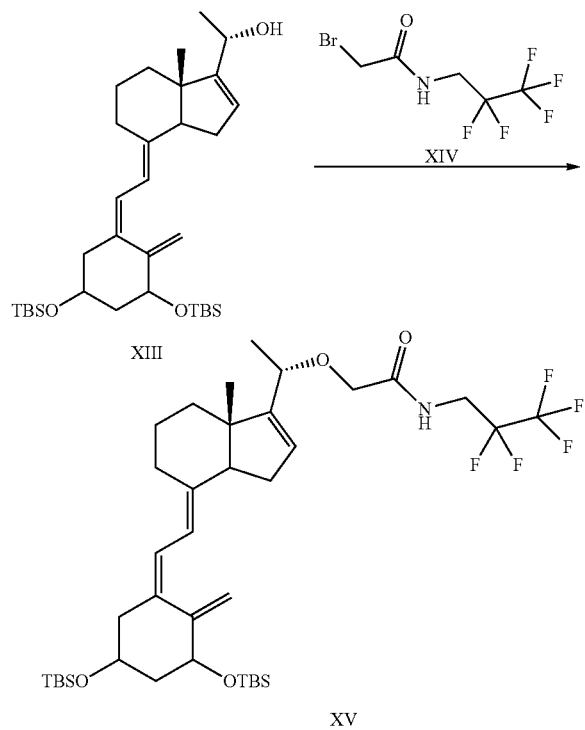

XIII

XV

Step (3) carrying out a reaction to remove the hydroxyl-protecting group on the compound XV with the reagent for removing the hydroxyl-protecting group in an organic solvent to obtain Pefcalcitol XVI;

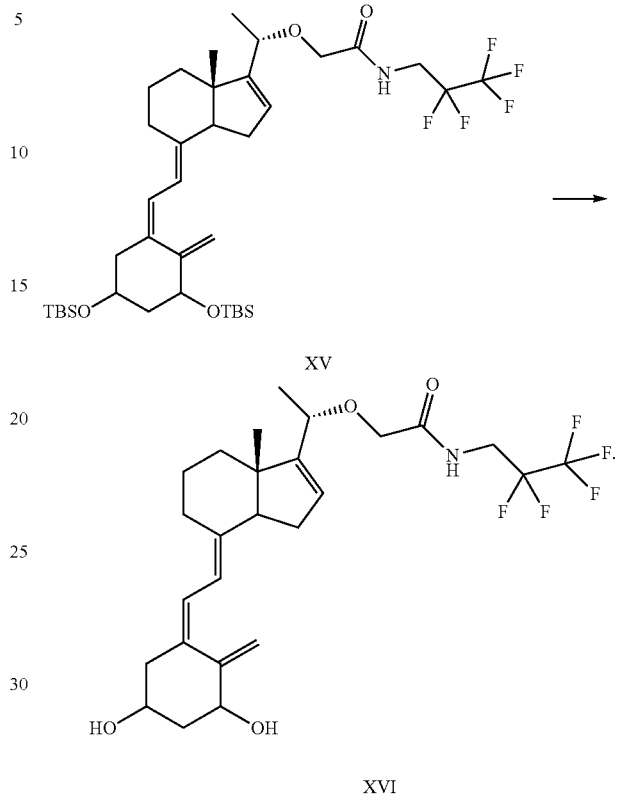

XV

XVI

In step (1), the preparation method of the compound XIII can be carried out by a conventional method of the ring-opening reaction in the art, and the following reaction methods and conditions are particularly preferred in the present invention:

In the preparation method of the compound XIII, the organic solvent is preferably an aromatic hydrocarbon solvent, and the aromatic hydrocarbon solvent is preferably one or more of benzene, toluene and xylene, and more preferably toluene.

In the preparation method of the compound XIII, the volume-to-mass ratio of the organic solvent to the compound I is preferably 2 mL/g-20 mL/g, more preferably 5 mL/g-10 mL/g.

In the preparation of the compound XIII, the aluminum salt catalyst is preferably one or more of aluminum triisopropoxide, aluminum tri-sec-butoxide and aluminum tri-t-butoxide, and more preferably aluminum triisopropoxide.

In the preparation method of the compound XIII, the molar ratio of the aluminum salt catalyst to the compound I is preferably 0.01-0.5, and more preferably 0.1-0.3.

In the preparation method of the compound XIII, the temperature of the ring-opening reaction is preferably 80° C. to 150° C., and more preferably 100° C. to 120° C.

In the preparation of the compound XIII, the progress of the ring-opening reaction can be monitored using conventional monitoring methods (e.g., TLC, HPLC or NMR) in the art, generally considering the disappearance of compound I as the end of the reaction. The ring-opening reaction time is preferably 1 h-10 h, and more preferably 1 h-3 h.

The preparation of the compound XIII is preferably carried out in the presence of an inert gas, and when the preparation of the compound XIII is carried out in the presence of an inert gas, the inert gas is preferably one or more of nitrogen, helium, argon, neon, krypton and xenon, and more preferably nitrogen and/or argon.

In the present invention, the compound XIV is prepared by an addition reaction of bromoacetyl bromide and pentafluoropropionamide according to the method described in patent application EP 1955999A1.

The preparation method of the compound XIII preferably comprises the post-treatment steps of: after completion of the reaction, adding a solvent, removing the aluminum salt, washing and drying the organic phase, removing the solvent and separating by the column chromatography to obtain purified compound XIII. The solvent in "adding a solvent" is preferably an alkane solvent, and the alkane solvent is preferably n-heptane. The "removing the aluminum salt" is preferably using dilute sulfuric acid to wash, the concentration of the dilute sulfuric acid is preferably 0.5 M-2 M, the concentration refers to the ratio of the molar amount of dilute sulfuric acid to the total volume of the dilute sulfuric acid. The solvent used for the column chromatography is preferably a mixed solvent of an ester solvent and an alkane solvent, and the volume ratio of the ester solvent to the alkane solvent is preferably 1:20-1:1, more preferably 1:10-1:5. The ester solvent is preferably ethyl acetate, and the alkane solvent is preferably n-heptane.

In step (2), the preparation method of the compound XV may be a conventional method for a nucleophilic substitution reaction in the art, and the following reaction methods and conditions are particularly preferred in the present invention:

In the preparation method of the compound XV, the organic solvent is preferably an ether solvent and/or an amide solvent, and the ether solvent is preferably tetrahydrofuran (THF); and the amide solvent is preferably N,N-dimethylformamide (DMF).

In the preparation method of the compound XV, the volume-to-mass ratio of the organic solvent to the compound XIII is preferably 1 mL/g-20 mL/g, and more preferably 3 mL/g-10 mL/g.

In the preparation of the compound XV, the base is preferably an inorganic base and/or an organic base, and the inorganic base is preferably one or more of sodium hydride (NaH), potassium hydride (KH) and potassium tert-butoxide (KOtBu); the organic base is preferably one or more of lithium hexamethyldisilazide (LiHMDS), sodium hexamethyldisilazide (NaHMDS) and potassium hexamethyldisilazide (KHMDS).

In the preparation method of the compound XV, the molar ratio of the base to the compound XIII is preferably 1-5, more preferably 2-3.

In the preparation method of the compound XV, the molar ratio of the compound XIV to the compound XIII is preferably 0.8-3, more preferably 1-1.5.

In the preparation method of the compound XV, the temperature of the nucleophilic substitution reaction is preferably $-20°$ C. to $0°$ C., more preferably $-15°$ C. to $-5°$ C.

In the preparation method of the compound XV, the progress of the nucleophilic substitution reaction may be monitored using conventional monitoring methods (e.g., TLC, HPLC or NMR) in the art, generally considering the disappearance of compound XIII as the end of the reaction, and the reaction time for the nucleophilic substitution reaction is preferably 10 min-5.0 h, and more preferably 30 min-60 min.

The preparation of the compound XV is preferably carried out in the presence of an inert gas, and when the preparation of the compound XV is carried out in the presence of an inert gas, the inert gas is preferably one or more of nitrogen, helium, argon, neon, krypton and xenon, and more preferably nitrogen and/or argon.

The preparation method of the compound XV preferably comprises the steps of: adding a mixture of compound XIII and an organic solvent into a mixture of a base and an organic solvent at a temperature of $-20°$ C. to $-15°$ C., reacting for 10 min-20 min, then adding a mixture of the compound XIV and an organic solvent, reacting to obtain the compound XV. The adding method is preferably dripping, with such a speed that the temperature of the reaction system is not more than $-5°$ C.

The preparation method of the compound XV preferably comprises the post-treatment steps of: after the completion of the reaction, quenching the reaction, extracting, washing, removing the organic solvent from the organic phase, separating by column chromatography to obtain the purified polyene compound I. The reagent used in the quenching reaction is preferably a saturated $NH_4Cl$ solution. The extraction may be carried out by a conventional method of operation in the art, and the solvent used for the extraction is preferably an alkane solvent, and the alkane solvent is preferably n-heptane. The separation by column chromatography may be carried out by conventional methods of operation in the art, the solvent used for column chromatography is preferably a mixed solvent of an ester solvent and an alkane solvent, the volume ratio of the ester solvent to the alkane solvent is preferably 1:20-1:1, more preferably 1:8-1:5. The ester solvent is preferably ethyl acetate, and the alkane solvent is preferably n-heptane or n-hexane.

In step (3), the preparation method of the Pefcalcitol XVI may be a conventional method for removing the hydroxy-protecting group in the art, and the following reaction methods and conditions are particularly preferred in the present invention:

In the preparation method of Pefcalcitol XVI, the organic solvent is preferably an ether solvent, and the ether solvent is preferably tetrahydrofuran.

In the preparation method of Pefcalcitol XVI, the volume-to-mass ratio of the organic solvent to the compound XV is preferably 5 mL/g-20 mL/g, more preferably 5 mL/g-10 mL/g.

In the preparation method of Pefcalcitol XVI, the reagent for removing the hydroxy-protecting group is preferably tetrabutylammonium fluoride or hydrofluoric acid.

In the preparation method of Pefcalcitol XVI, the molar ratio of the reagent for removing the hydroxy-protecting group to the compound XV is preferably 2-10, more preferably 3-6.

In the preparation method of Pefcalcitol XVI, the temperature of the reaction for removing the hydroxyl-protecting group is preferably $0°$ C. to $50°$ C., and more preferably $35°$ C. to $45°$ C.

In the preparation method of Pefcalcitol XVI, the process of the reaction to remove the hydroxy-protecting group may be monitored using conventional monitoring methods (e.g., TLC, HPLC or NMR) in the art, and generally considering the disappearance of the compound XV as the end of the reaction, the reaction time to remove the hydroxy-protecting group is preferably 1 h-10 h, and more preferably 5 h-8 h.

The preparation method of the Pefcalcitol XVI is preferably carried out in the presence of an inert gas, and when the preparation method of the Pefcalcitol XVI is carried out in the presence of an inert gas, the inert gas is preferably one or more of nitrogen, helium, argon, neon, krypton and xenon, and more preferably nitrogen and/or argon.

The preparation method of Pefcalcitol XVI preferably comprises the post-treatment steps of: after the completion of the reaction, extracting, washing and drying the reaction solution, removing the solvent, purifying by column chromatography and/or recrystallization to obtain purified Pefcalcitol XVI. The extraction may be carried out by a conventional method of operation in the art, and the solvent used for the extraction is preferably an ester solvent, and the ester solvent is preferably ethyl acetate. The separation by column chromatography may be carried out by conventional methods of operation in the art. The solvent used for column chromatography is preferably a mixed solvent of an ester solvent and an alkane solvent, the volume ratio of the ester solvent to the alkane solvent is preferably 1:10-10:1, further preferably 1:2-2:1. The ester solvent is preferably ethyl acetate, and the alkane solvent is preferably n-heptane. The recrystallization may be carried out by conventional methods of operation in the art. The solvent used for recrystallization is preferably a mixed solvent of an ester solvent and an alkane solvent, and the volume ratio of the ester solvent to the alkane solvent is preferably 1:10-10:1, and more preferably 1:2-2:1

The present invention also provides a preparation method of the compound XV, which comprises the following steps:

Step ①: carrying out a ring-opening reaction on the polyene compound I under the presence of an aluminum salt catalyst and in an organic solvent to obtain the compound XIII;

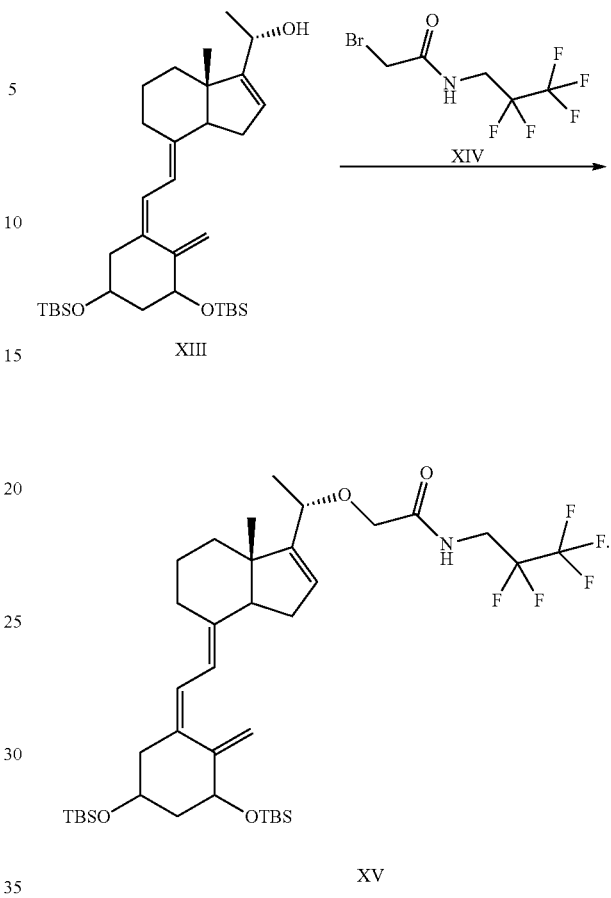

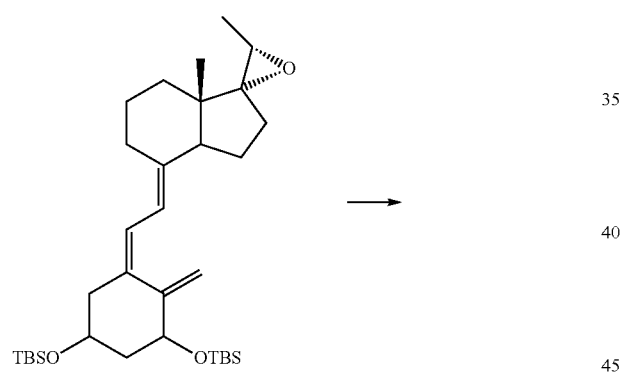

Step ②: carrying out a nucleophilic substitution reaction on the compound XIII with the compound XIV in the presence of a base and in an organic solvent to obtain the compound XV;

Wherein, each of the reaction conditions is as described in step (1) and step (2) of the preparation method of Pefcalcitol XVI.

The present invention also provides a preparation method of the compound XIII, which comprises the following steps: carrying out a ring-opening reaction on the polyene compound I in the presence of an aluminum salt catalyst and in an organic solvent to obtain the compound XIII;

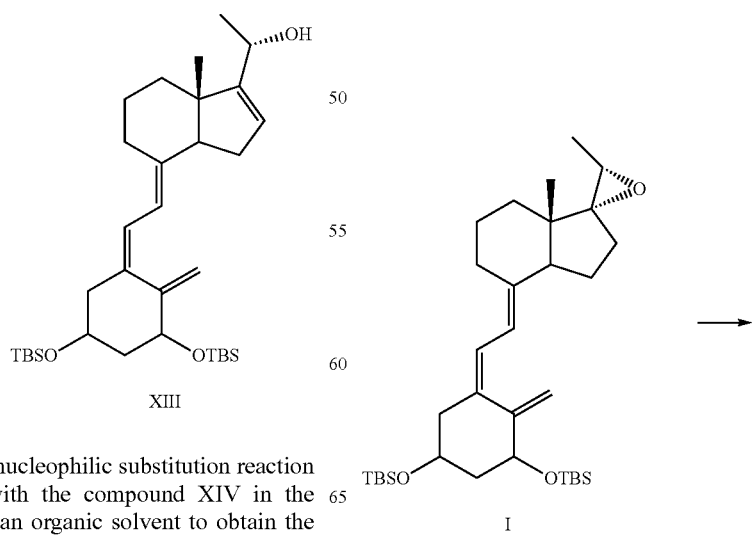

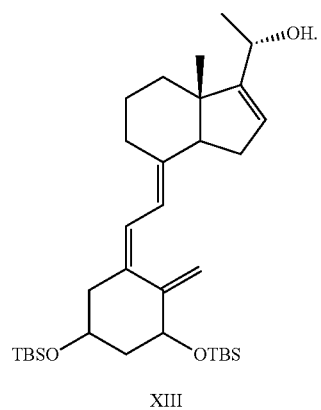
XIII
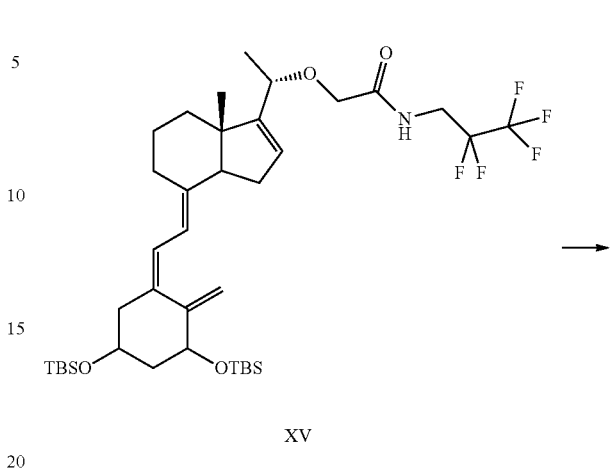
XV
Wherein each of the reaction conditions is as described in step (1) of the preparation method of Pefcalcitol XVI.
In the present invention, the preparation method of Pefcalcitol XVI preferably comprises the following synthetic route:
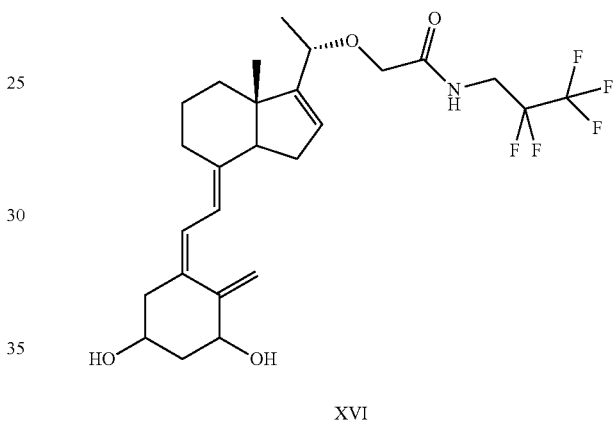
XVI
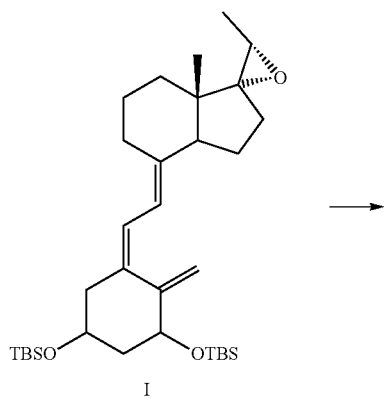
I
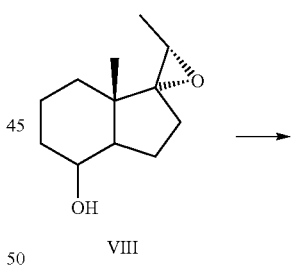
VIII
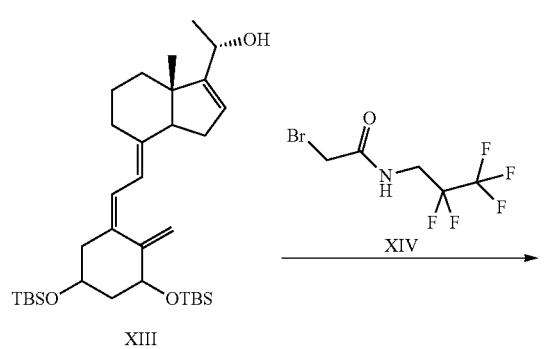
XIII    XIV
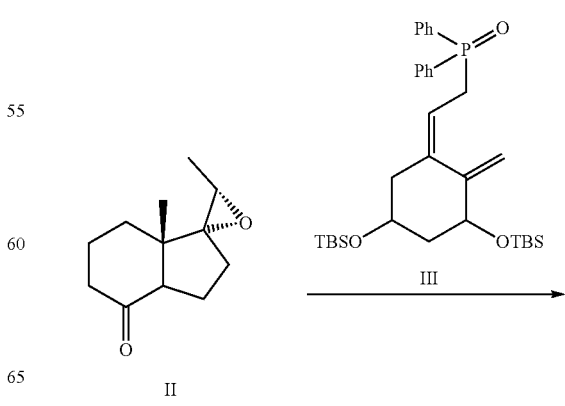
II    III

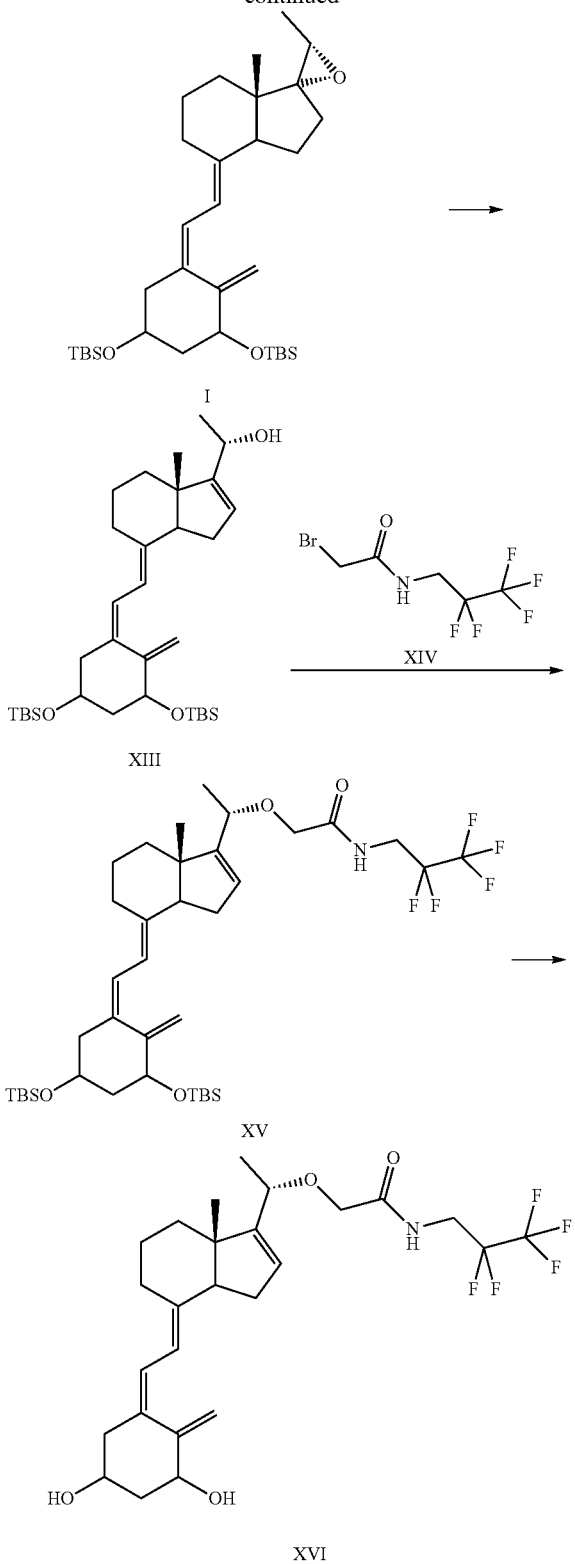

In the present invention, the preparation method of Pefcalcitol XVI more preferably comprises the following synthetic route:

The above preferred conditions of the present invention may be arbitrarily combined without departing from the general knowledge in the art to obtain the preferred examples of the present invention.

The reagents and raw materials used in the present invention are commercially available.

In the present invention, the room temperature refers to an ambient temperature of 20° C. to 25° C.

The advantages of the present invention lies in that: the preparation method of the present invention has simple operation, mild reaction condition, no heavy metal involved, no obvious by-product, high reaction conversion rate, high yield, high purity of the product, simple post-treatment and is suitable for industrial production.

DETAILED DESCRIPTION OF THE PREFERRED EMBODIMENT

The following examples further illustrate the present invention, but the present invention is not limited thereto. The experimental methods not specified in the following examples are selected according to conventional methods and conditions, or in accordance with the product specifications.

Example 1: Preparation of the Compound II

Oxalyl chloride (15.7 mL) and anhydrous dichloromethane (DCM, 300 mL) were added into a three-necked flask (1 L) under nitrogen atmosphere and cooled in a dry ice bath to a temperature of −60° C. to −70° C. The solution of DMSO (0.36 mol, 3 eq, 24.5 mL) and DCM (20 mL) was slowly added dropwise, and stirred for 30 min after the completion of the dropwise addition. The solution of the raw material VIII (23.5 g) and DCM (40 mL) was slowly added dropwise with temperature controlled below −60° C., and stirred for 60 min after the completion of the dropwise addition. Triethylamine (Et$_3$N, 75 mL) was slowly added dropwise with temperature controlled below −60° C. After the completion of the dropwise addition, the temperature was raised to 0° C. naturally. Thereafter, the reaction was carried out until completion of the reaction, as monitored by TLC. Saturated ammonium chloride aqueous solution was added to quench the reaction. The phases were separated. The aqueous phase was extracted twice with DCM. The organic layer was combined, washed with brine, dried and concentrated to yield an oily matter (24.0 g). The oily matter was dried under vacuum for 3 h by an oil pump, and used in the next step directly. The crude yield was 100%. A small amount of product was purified by column chromatography, and the sample was sent for the measurement of $^1$H NMR, which was consistent with the data of Example 2 on page 17 of the patent document EP 1955999A1.

Example 2: Preparation of the Compound II

The raw material VIII (10 g) and DCM (100 mL) were added into a three-necked flask (500 mL), dissolved and cooled in a dry ice bath to a temperature of 5° C. to 10° C. PCC oxidizer was added in batches. The reaction was carried out until complete conversion of raw materials as monitored by TLC. The solution was filtered, washed, dried and concentrated to yield an oily matter (9.2 g). The oily matter was dried under vacuum for 3 h by an oil pump, and used in the next step directly.

Example 3: Preparation of the Compound I

Under nitrogen atmosphere, the compound II (10 mmol, 1.0 eq, 1.94 g) and the compound III (12 mmol, 1.2 eq, 7.0 g) were mixed, dissolved in dry THF (tetrahydrofuran) (30 mL) and cooled in a dry ice bath to a temperature of −60° C. to −70° C. A solution of lithium hexamethyldisilazide (LiHMDS) (1.0 M/L, 12 mmol, 1.2 eq, 11 mL) was added dropwise, and the reaction solution was bright red. The reaction was carried out for 90 min. During the process, LiHMDS solution (1.0 mL) was recharged when the solution color faded, so the total consumption is 12 mL until completion of the reaction as monitored by TLC. The reaction solution was diluted with ethyl acetate and saturated ammonium chloride aqueous solution, then the phases were separated. The aqueous phase was extracted twice with ethyl acetate. The organic layer was combined, washed with brine, and extracted by reversed phase once. The organic layer was combined, dried, concentrated and separated by column chromatography (n-heptane:ethyl acetate=10:1 by volume, as eluent) to yield a foam (4.75 g) with a yield of 85.2% and an HPLC purity of 95.1%.

$^1$H NMR (400 MHz, CDCl$_3$) δ: 6.24 (d, J=11.2 Hz, 1H), 6.07 (d, J=11.2 Hz, 1H), 5.19 (m, 1H), 4.88 (m, 1H), 4.38 (m, 1H), 4.19 (m, 1H), 2.99 (m, 1H), 2.83 (m, 1H), 2.50-2.38 (m, 2H), 2.24-2.15 (m, 2H), 1.90-1.40 (m, 10H), 1.37 (d, J=5.6 Hz, 3H), 0.85 (s, 18H), 0.75 (s, 3H), 0.06 (s, 12H).

Example 4: Preparation of the Compound I

The compound II (10.3 mmol, 1.0 eq, 2.00 g) and the compound III (12 mmol, 1.2 eq, 7 g) were mixed, dissolved in dry THF (tetrahydrofuran) (30 mL) and cooled in a dry ice bath to a temperature of −60° C. to −70° C. A solution of sodium hexamethyldisilazide (NaHMDS) (1.0 MIL, 12 mmol, 1.2 eq, 12 mL) was added dropwise, and the reaction solution was bright red. The reaction was carried out for 90 min until completion of the reaction as monitored by TLC. The reaction solution was diluted with ethyl acetate and saturated ammonium chloride aqueous solution, then separated. The aqueous phase was extracted twice with ethyl acetate. The organic layer was combined, washed with brine, and extracted by reversed phase once. The organic layer was combined, dried, concentrated and purified by column chromatography (n-heptane:ethyl acetate=10:1 by volume, as eluent) to yield an oily matter (4.61 g) with a yield of 82.6% and a HPLC purity of 96.3%. $^1$H NMR data is the same as in Example 3.

Example 5: Preparation of the Compound I

Under nitrogen atmosphere, the compound III (6.9 mmol, 1.25 eq, 4.0 g) was dissolved in dry THF (tetrahydrofuran) (40 mL) and cooled to a temperature of −60° C. to −70° C. A solution of potassium hexamethyldisilazide (KHMDS) (1.0 M, 6.3 mL) was added dropwise, and the reaction solution was bright red. After stirring at low temperature for 10 min, a solution of the compound II (5.7 mmol, 1.0 eq, 1.10 g) in THF (tetrahydrofuran) (10 mL) was added dropwise, and the reaction was carried out for 90 min. The reaction solution was diluted with ethyl acetate and saturated ammonium chloride aqueous solution, then phases were separated. The aqueous phase was extracted twice with ethyl acetate. The organic layer was combined, washed with brine, and extracted by reversed phase once. The organic layer was combined, dried, concentrated and separated by column chromatography (n-heptane:ethyl acetate=10:1 by volume, as eluent) to yield a foam (2.69 g) with a yield of 84.3% and a HPLC purity of 94.2%. $^1$H NMR data is the same as in Example 3.

Example 6: Preparation of the Compound I

Under nitrogen atmosphere, the compound III (6.9 mmol, 1.33 eq, 4.0 g) was dissolved in dry THF (tetrahydrofuran) (40 mL) and cooled to a temperature of −40° C. to −50° C. in a dry ice bath. The solution of Lithium hexamethyldisilazide (LiHMDS) (1.0 M, 6.9 mL) was added dropwise, and the reaction solution was bright red. After stirring at low temperature for 10 min, a solution of the compound II (5.18 mmol, 1.0 eq, 1.00 g) in THF (tetrahydrofuran) (10 mL) was added dropwise, and the reaction was carried out for 2 h. The reaction solution was diluted with ethyl acetate and saturated ammonium chloride aqueous solution, then the phases were separated. The aqueous phase was extracted twice with ethyl acetate. The organic layer was combined, washed with brine, and extracted by reversed phase once. The organic layer was combined, dried, concentrated and separated by column chromatography (n-heptane:ethyl acetate=10:1 by volume, as eluent) to yield a foam (2.52 g) with a yield of 87.1% and an HPLC purity of 93.0%. $^1$H NMR data is the same as in Example 3.

Example 7: Preparation of Compound XIII

The compound I (9.0 g) was dissolved in anhydrous toluene (90 mL), and aluminum triisopropoxide (400 mg) was added under nitrogen atmosphere. The temperature was raised to 120° C. to reflux for 1 h-3 h. After the reaction was complete as monitored by TLC, the mixture was cooled to room temperature. The reaction solution was diluted by adding n-heptane (360 mL) and the dilute sulfuric acid (0.5 M) was added to wash off the aluminum salt. The phases were separated. The organic phase was washed successively with NaHCO$_3$ solution and brine, dried and desolvated, and then purified by column chromatography with ethyl acetate: n-heptane (1:10) by volume to obtain the compound XIII (7.9 g) as shown in formula (XIII), as a pale yellow foamy solid with a HPLC purity of 96.7% and yield of 88%.

$^1$H NMR (400 MHz, CDCl$_3$) δ: 6.21 (d, J=11.2 Hz, 1H), 6.07 (d, J=11.2 Hz, 1H), 5.61 (t, 1H), 5.15 (m, 1H), 4.84 (m, 1H), 4.38 (m, 2H), 4.16 (m, 1H), 2.78 (m, 1H), 2.45-2.30 (m, 2H), 2.24-2.15 (m, 2H), 2.04-1.96 (m, 1H), 1.90-1.60 (m, 6H), 1.56-1.46 (m, 2H), 1.32 (d, J=6.4 Hz, 3H), 0.86 (s, 18H), 0.76 (s, 3H), 0.06 (s, 12H).

Example 8: Preparation of the Compound XIII

The compound I (5.0 g) was dissolved in anhydrous xylene (50 mL), and aluminum tri-sec-butoxide (300 mg) was added under nitrogen atmosphere. The temperature was raised to 120° C. to reflux for 2 h-3 h. After the reaction was complete as monitored by TLC, the mixture was cooled to room temperature. The reaction solution was diluted by adding n-heptane (250 mL) and the dilute sulfuric acid (0.5 M) was added to wash off the aluminum salt. The phases were separated. The organic phase was washed successively with NaHCO$_3$ solution and brine, dried and desolvated, and then purified by column chromatography with ethyl acetate: n-heptane (1:10) by volume to obtain the compound XIII (4.5 g) as shown in formula (XIII), as a pale yellow foam with a HPLC purity of 95.2% and yield of 90%.

Example 9: Preparation of the Compound XV

A solution of NaHMDS in tetrahydrofuran (1.0 M, 10 mL) was added into a flask (50 mL) and cooled to −15° C. in cold bath under nitrogen atmosphere, then a solution of the compound XIII (4.4 mmol, 2.50 g) and re-evaporated DMF (4 mL) was added dropwise and stirred for 10 min. A solution (4 mL) of the compound XIV (1.30 g) in DMF was added dropwise, slowly heated to −5° C. to react for half an hour, and a saturated ammonium chloride solution (10 mL) was added to terminate the reaction. The reaction system was diluted with n-heptane (50 mL) and stirred to separate phases. The organic phase was washed successively with water and saturated sodium chloride solution, dried, concentrated and purified by column chromatography (n-heptane:ethyl acetate=8:1 by volume, as eluent) to give an oily matter (2.84 g) with a HPLC purity of 95% and yield of 85%. The $^1$H NMR data is consistent with that reported in Example 29 of patent document EP 1955999A1.

Example 10: Preparation of Pefcalcitol

The compound XV (1.70 g) was dissolved in dry THF (tetrahydrofuran) (17 mL), tetrabutylammonium fluoride (3.40 g) was added and the temperature was raised to 35° C., reacting for 5 h under nitrogen atmosphere. Thereafter, a saturated aqueous ammonium chloride solution (30 mL) and ethyl acetate (30 mL) were added, stirred and separate phase. The aqueous phase was extracted twice with ethyl acetate. The organic layer was combined, washed with an ammonium chloride aqueous solution (20 mL) and brine (20 mL), extracted by reversed phase, dried over anhydrous sodium sulfate, concentrated and purified by chromatography column with ethyl acetate:n-heptane (1:1 by volume) to give a viscous material which was purified by crystallization to give a white solid with a HPLC purity of 99% or more and a yield of 85%. The $^1$H NMR data for the product is consistent with that reported in Example 22 on page 108 of patent document WO 0196293A1.

What is claimed is:

1. A polyene compound of the following structure I:

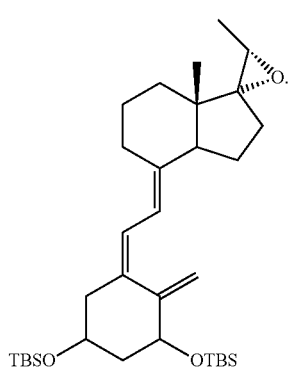

I

2. A preparation method of the polyene compound I according to claim 1, comprising the following steps: under an action of a base and in an organic solvent, conducting a Wittig-Horner reaction on the compound II and the compound III to obtain the polyene compound I;

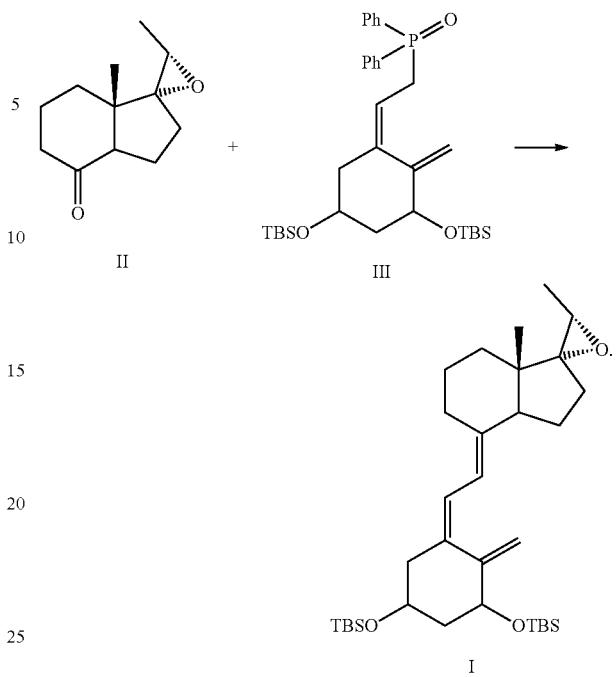

3. The preparation method of the polyene compound I according to claim 2, wherein:
in the preparation method of the polyene compound I, the organic solvent is an ether solvent;
or,
in the preparation method of the polyene compound I, the volume-to-mass ratio of the organic solvent to the compound II is 5 mL/g-50 mL/g;
or,
in the preparation method of the polyene compound I, the base is an organic base;
or,
in the preparation method of the polyene compound I, the molar ratio of the base to the compound II is 0.8-1.5;
or,
in the preparation method of the polyene compound I, the molar ratio of the compound III to the compound II is 0.8-1.5;
or,
in the preparation method of the polyene compound I, the temperature of the Wittig-Horner reaction is −80° C. to −50° C.;
or,
in the preparation method of the polyene compound I, the reaction time of the Wittig-Horner reaction is 0.5 h-5.0 h;
or,
the preparation method of the polyene compound I is carried out in the presence of an inert gas;
or,
the preparation method of the polyene compound I is carried out under anhydrous conditions;
or,
the preparation method of the polyene compound I comprises step 1 or step 2,
step 1: adding a base into a solution formed by the compound III and an organic solvent at a temperature of −60° C. to −70° C. under an inert gas, reacting for 10 min-30 min, then adding a mixture of the compound II and an organic solvent to carry out Wittig-Horner reaction to obtain the polyene compound I;

step 2: adding a base into a solution formed by the compound II, the compound III and an organic solvent at a temperature of −60° C. to −70° C. under an inert gas to carry out Wittig-Horner reaction to obtain the polyene compound I;

or, the preparation method of the polyene compound I comprises the post-treatment steps of: after the completion of the reaction, quenching the reaction, extracting, washing, removing the organic solvent from the organic phase, and separating by column chromatography to obtain the purified polyene compound I.

4. The preparation method of the polyene compound I according to claim 3, wherein:

in the preparation method of the polyene compound I, the ether solvent is one or more of tetrahydrofuran, methyltetrahydrofuran, and methyl tert-butyl ether;

or, in the preparation method of the polyene compound I, the volume-to-mass ratio of the organic solvent to the compound II is 15 mL/g-50 mL/g;

or, in the preparation method of the polyene compound I, the organic base is one or more of butyllithium, lithium hexamethyldisilazide, sodium hexamethyldisilazide, potassium hexamethyldisilazide and lithium diisopropylamide;

or, in the preparation method of the polyene compound I, the molar ratio of the base to the compound II is 0.9-1.3;

or, in the preparation method of the polyene compound I, the molar ratio of the compound III to the compound II is 1-1.3;

or, in the preparation method of the polyene compound I, the temperature of the Wittig-Horner reaction is −70° C. to −60° C.;

or, in the preparation method of the polyene compound I, the reaction time of the Wittig-Horner reaction is 1.5 h-2.0 h;

or, when the preparation method of the polyene compound I is carried out in the presence of an inert gas, the inert gas is one or more of nitrogen, helium, argon, neon, krypton and xenon;

or, in step 1 or step 2, the adding method is dripping, with such a speed that the temperature of the reaction system is not more than −60° C.;

or, in the post-treatment step of the preparation method of the polyene compound I, the reagent used in the quenching reaction is a saturated NH$_4$Cl solution;

or, in the post-treatment step of the preparation method of the polyene compound I, the solvent used for the extraction is an ester solvent;

or, in the post-treatment step of the preparation method of the polyene compound I, the solvent used for column chromatography is a mixed solvent of an ester solvent and an alkane solvent, and the volume ratio of the ester solvent to the alkane solvent is 1:5-1:20.

5. The preparation method of the polyene compound I according to claim 2, wherein: the preparation method of the polyene compound I further comprises reacting the compound VIII with an oxidizing agent in an organic solvent to obtain the compound II;

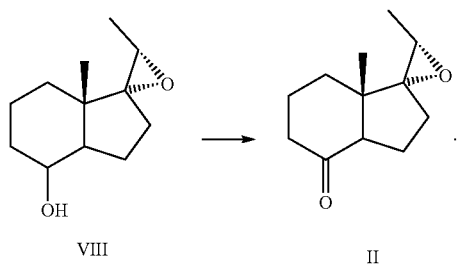

6. The preparation method of the polyene compound I according to claim 5, wherein:

in the preparation method of the compound II, the organic solvent is a halogenated hydrocarbon solvent;

or, in the preparation method of the compound II, the volume-to-mass ratio of the organic solvent to the compound VIII is 5 mL/g-20 mL/g;

or, in the preparation method of the compound II, the oxidizing agent is one of pyridine chromium oxide complex, pyridinium dichromate, 1,1,1-triacetoxy-1,1-dihydro-1,2-benziodoxol-3-(1H)-one, sodium hypochlorite, or oxalyl chloride-dimethyl sulfoxide oxidant;

or, in the preparation method of the compound II, the molar ratio of the oxidizing agent to compound VIII is 1-5;

or, in the preparation method of the compound II, the temperature of the oxidation reaction is −80° C. to 50° C.;

or, in the preparation method of the compound II, the reaction time of the oxidation reaction is 0.5 h-5.0 h;

or, in the preparation method of the compound II is carried out in the presence of an inert gas;

or, the preparation method of the compound II comprises the following post-treatment steps: after the completion of the reaction, quenching the reaction, extracting, washing and drying the reaction solution, removing the solvent to obtain the purified compound II.

7. The preparation method of the polyene compound I according to claim 6, wherein:

in the preparation method of the compound II, the halogenated hydrocarbon solvent is a chlorinated hydrocarbon solvent;

or, in the preparation method of the compound II, the volume-to-mass ratio of the organic solvent to the compound VIII is 7 mL/g-15 mL/g;

or, in the preparation method of the compound II, the molar ratio of the oxidizing agent to the compound VIII is 3-4;

or, in the preparation method of the compound II, when the oxidizing agent is the oxalyl chloride-dimethyl sulfoxide oxidant, the oxidation reaction is carried out in the presence of a base; the molar ratio of the base to compound VIII is 1-5;

or, in the preparation method of the compound II, when the oxidizing agent is the oxalyl chloride-dimethyl sulfoxide oxidant, the molar ratio of the dimethyl sulfoxide to the oxalyl chloride is 1-10, the molar ratio of the dimethyl sulfoxide to the compound VIII is 1-5;

or, in the preparation method of the compound II, when the oxidizing agent is the oxalyl chloride-dimethyl sulfoxide oxidant, the temperature of the oxidation reaction is −70° C. to −60° C.;

or, in the preparation method of the compound II, when the oxidizing agent is the pyridine chromium oxide complex, pyridinium dichromate, or 1,1,1-triacetoxy-1,1-dihydro-1,2-benziodoxol-3-(1H)-one, the temperature of the oxidation reaction is 0° C. to 50° C.;

or, in the preparation method of the compound II, the reaction time of the oxidation reaction is 1.5 h-2.0 h;

or, when the preparation method of the polyene compound II is carried out in the presence of an inert gas, the inert gas is one or more of nitrogen, helium, argon, neon, krypton and xenon;

or, in the preparation method of the compound II, when the oxidizing agent is the oxalyl chloride-dimethyl sulfoxide oxidant, the oxidation reaction comprises the steps of: adding a solution formed by DMSO and an organic solvent into a solution formed by oxalyl chloride and an organic solvent at a temperature of −70° C. to −60° C. under an inert gas, reacting for 0.5 h-1 h; adding a solution formed by the compound VIII and an organic solvent, reacting for 0.5 h-1 h; then adding a base to carry out an oxidation reaction to obtain the compound II.

8. A preparation method of Pefcalcitol XVI, comprising the following steps:

step (1): carrying out a ring-opening reaction on the polyene compound I in the presence of an aluminum salt catalyst and in an organic solvent to obtain the compound XIII;

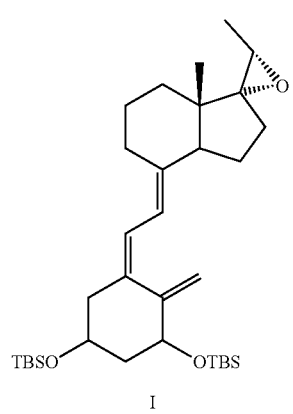

I

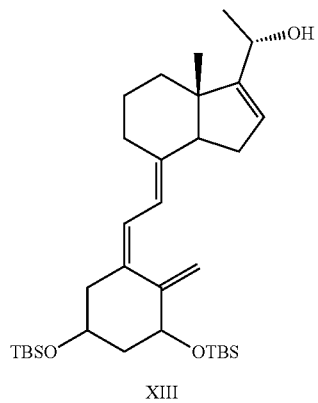

XIII step (2): carrying out a nucleophilic substitution reaction on the compound XIII with the compound XIV in the presence of a base and in an organic solvent to obtain the compound XV;

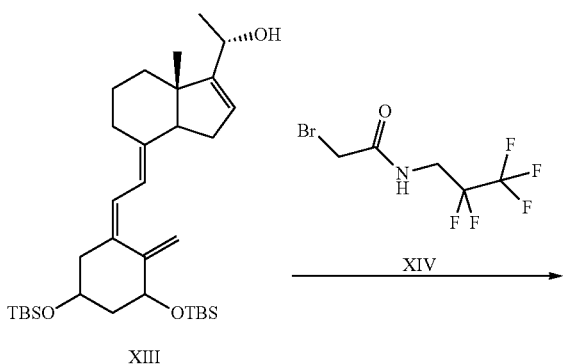

XIII

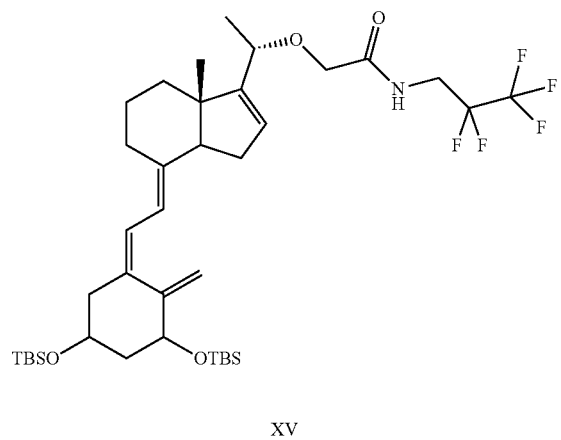

XV step (3): carrying out a reaction to remove the hydroxyl-protecting group on the compound XV with the reagent for removing the hydroxyl-protecting group in an organic solvent to obtain Pefcalcitol XVI;

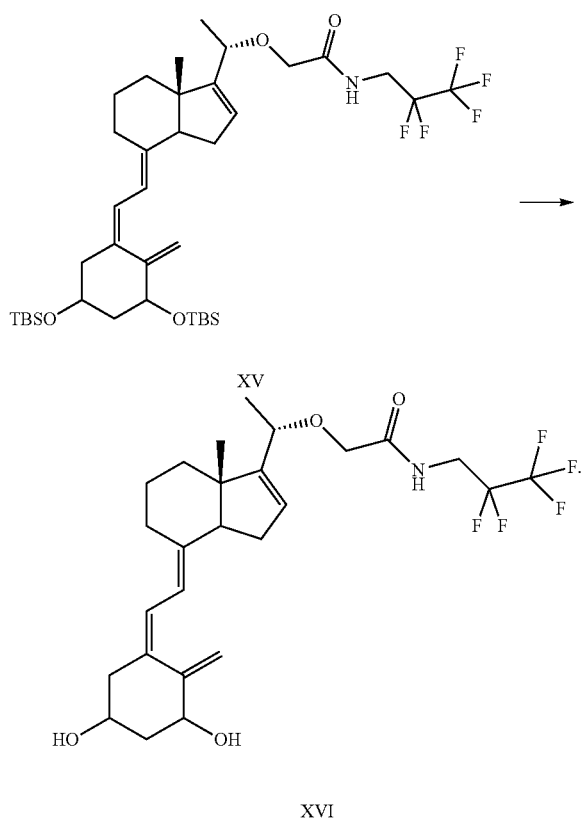

9. The preparation method of Pefcalcitol XVI according to claim 8, wherein:
in the preparation method of the compound XIII, the organic solvent is an aromatic hydrocarbon solvent;
or,
in the preparation method of the compound XIII, the volume-to-mass ratio of the organic solvent to the compound I is 2 mL/g-20 mL/g;
or,
in the preparation method of compound XIII, the aluminum salt catalyst is one or more of aluminum triisopropoxide, aluminum tri-sec-butoxide and aluminum tri-t-butoxide;
or,
in the preparation method of the compound XIII, the molar ratio of the aluminum salt catalyst to the compound I is 0.01-0.5;
or,
in the preparation method of the compound XIII, the temperature of the ring-opening reaction is 80° C. to 150° C.;
or,
in the preparation method of the compound XIII, the reaction time of the ring-opening reaction is 1 h-10 h;
or,
The preparation of the compound XIII is carried out in the presence of an inert gas;
or,
in the preparation method of the compound XV, the organic solvent is an ether solvent and/or an amide solvent;
or,
in the preparation method of the compound XV, the volume-to-mass ratio of the organic solvent to the compound XIII is 1 mL/g-20 mL/g;
or,
In the preparation method of the compound XV, the base is an inorganic base and/or an organic base;
or,
in the preparation method of the compound XV, the molar ratio of the base to the compound XIII is 1-5;
or,
in the preparation method of the compound XV, the molar ratio of the compound XIV to the compound XIII is 0.8-3;
or,
in the preparation method of the compound XV, the temperature of the nucleophilic substitution reaction is −20° C. to 0° C.;
or,
in the preparation method of the compound XV, the reaction time of the nucleophilic substitution reaction is 10 min-5.0 h;
or,
the preparation of the compound XV is carried out in the presence of an inert gas;
or,
the preparation method of the compound XV comprises the following steps: adding a mixture of the compound XIII and an organic solvent into a mixture of a base and an organic solvent at a temperature of −20° C. to −15° C., reacting for 10 min-20 min, then adding a mixture of the compound XIV and the organic solvent, reacting to obtain the compound XV;
or,
in step (3) of the preparation method of Pefcalcitol XVI, the organic solvent is an ether solvent;
or,
in the preparation method of Pefcalcitol XVI, the volume-to-mass ratio of the organic solvent to the compound XV is 5 mL/g-20 mL/g;
or,
in the preparation method of Pefcalcitol XVI, the reagent for removing the hydroxy-protecting group is tetrabutylammonium fluoride or hydrofluoric acid;
or,
in the preparation method of Pefcalcitol XVI, the molar ratio of the reagent for removing the hydroxy-protecting group to the compound XV is 2-10;
or,
in the preparation method of Pefcalcitol XVI, the temperature of the reaction for removing the hydroxyl-protecting group is 0° C. to 50° C.;
or,
In the preparation method of Pefcalcitol XVI, the reaction time to remove the hydroxy-protecting group is 1 h-10 h;
or,
the preparation method of the Pefcalcitol XVI is carried out in the presence of an inert gas.

10. The preparation method of the Pefcalcitol XVI according to claim 9, wherein:
in the preparation method of the compound XIII, the aromatic hydrocarbon solvent is one or more of benzene, toluene and xylene;
or,
in the preparation method of the compound XIII, the volume-to-mass ratio of the organic solvent to the compound I is 5 mL/g-10 mL/g;

or,
in the preparation method of the compound XIII, the molar ratio of the aluminum salt catalyst to the compound I is 0.1-0.3;
or,
in the preparation method of the compound XIII, the temperature of the ring-opening reaction is 100° C. to 120° C.;
or,
in the preparation method of the compound XIII, the reaction time of the ring-opening reaction is 1 h-3 h;
or,
when the preparation of the compound XIII is carried out in the presence of an inert gas, the inert gas is one or more of nitrogen, helium, argon, neon, krypton and xenon;
or,
in the preparation method of the compound XV, the ether solvent is tetrahydrofuran;
or,
in the preparation method of the compound XV, the amide solvent is N,N-dimethylformamide;
or,
in the preparation method of the compound XV, the volume-to-mass ratio of the organic solvent to the compound XIII is 3 mL/g-10 mL/g;
or,
In the preparation method of the compound XV, the inorganic base is one or more of sodium hydride, potassium hydride and potassium tert-butoxide;
or,
in the preparation method of the compound XV, the organic base is one or more of lithium hexamethyldisilazide, sodium hexamethyldisilazide and potassium hexamethyldisilazide;
or,
In the preparation method of the compound XV, the molar ratio of the base to the compound XIII is 2-3;
or,
in the preparation method of the compound XV, the molar ratio of the compound XIV to the compound XIII is 1-1.5;
or,
in the preparation method of the compound XV, the temperature of the nucleophilic substitution reaction is −15° C. to −5° C.;
or,
in the preparation method of the compound XV, the reaction time of the nucleophilic substitution reaction is 30 min-60 min;
or,
when the preparation of the compound XV is carried out in the presence of an inert gas, the inert gas is one or more of nitrogen, helium, argon, neon, krypton and xenon;
or,
in step (3) of the preparation method of Pefcalcitol XVI, the ether solvent is tetrahydrofuran;
or,
in the preparation method of Pefcalcitol XVI, the volume-to-mass ratio of the organic solvent to the compound XV is 5 mL/g-10 mL/g;
or,
in the preparation method of Pefcalcitol XVI, the molar ratio of the reagent for removing the hydroxy-protecting group to the compound XV is 3-6;
or,
in the preparation method of Pefcalcitol XVI, the temperature of the reaction for removing the hydroxyl-protecting group is 35° C. to 45° C.;
or,
in the preparation method of Pefcalcitol XVI, the reaction time to remove the hydroxy-protecting group is 5 h-8 h;
or,
when the preparation method of the Pefcalcitol XVI is carried out in the presence of an inert gas, the inert gas is one or more of nitrogen, helium, argon, neon, krypton and xenon.

11. A preparation method of the compound XV, comprising the following steps:
step 1: carrying out a ring-opening reaction on the polyene compound I under the presence of an aluminum salt catalyst and in an organic solvent to obtain the compound XIII;

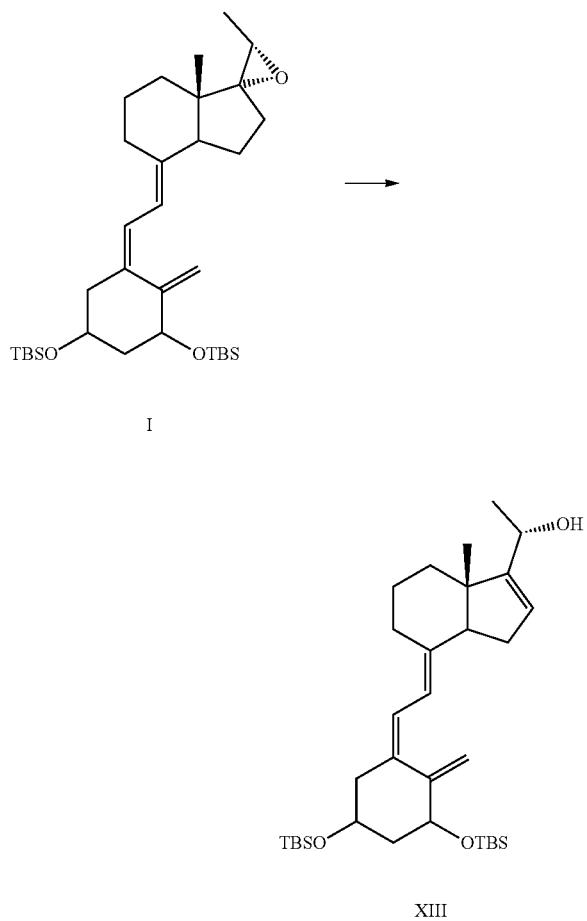

step 2: carrying out a nucleophilic substitution reaction on the compound XIII with the compound XIV in the presence of a base and in an organic solvent to obtain the compound XV;

33

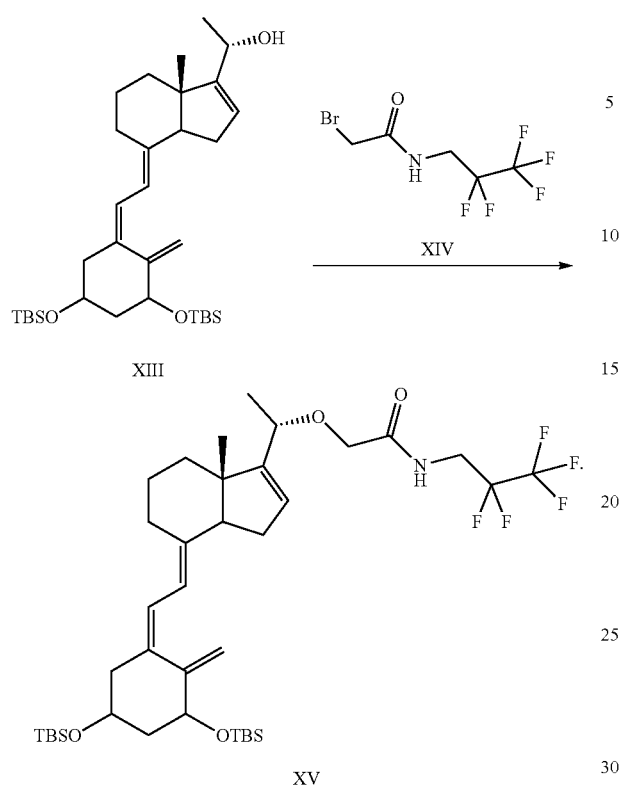

12. A preparation method of the compound XIII, comprising carrying out a ring-opening reaction on the polyene compound I in the presence of an aluminum salt catalyst and in an organic solvent to obtain the compound XIII;

34

13. The preparation method of the compound XV according to claim 11, comprising the following steps:

step 1: carrying out a ring-opening reaction on the polyene compound I under the presence of an aluminum salt catalyst and in the organic solvent to obtain the compound XIII;

step 2: carrying out a nucleophilic substitution reaction on the compound XIII with the compound XIV in the presence of a base and in an organic solvent to obtain the compound XV;

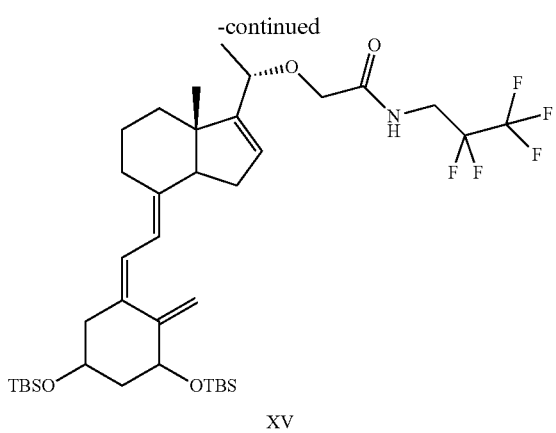

XV wherein,
in the preparation method of the compound XIII, the organic solvent is an aromatic hydrocarbon solvent;
or,
in the preparation method of the compound XIII, the volume-to-mass ratio of the organic solvent to the compound I is 2 mL/g-20 mL/g;
or,
in the preparation method of compound XIII, the aluminum salt catalyst is one or more of aluminum triisopropoxide, aluminum tri-sec-butoxide and aluminum tri-t-butoxide;
or,
in the preparation method of the compound XIII, the molar ratio of the aluminum salt catalyst to the compound I is 0.01-0.5;
or,
in the preparation method of the compound XIII, the temperature of the ring-opening reaction is 80° C. to 150° C.;
or,
in the preparation method of the compound XIII, the reaction time of the ring-opening reaction is 1 h-10 h;
or,
The preparation of the compound XIII is carried out in the presence of an inert gas;
or,
in the preparation method of the compound XV, the organic solvent is an ether solvent and/or an amide solvent;
or,
in the preparation method of the compound XV, the volume-to-mass ratio of the organic solvent to the compound XIII is 1 mL/g-20 mL/g;
or,
In the preparation method of the compound XV, the base is an inorganic base and/or an organic base;
or,
in the preparation method of the compound XV, the molar ratio of the base to the compound XIII is 1-5;
or,
in the preparation method of the compound XV, the molar ratio of the compound XIV to the compound XIII is 0.8-3;
or,
in the preparation method of the compound XV, the temperature of the nucleophilic substitution reaction is −20° C. to 0° C.;
or, in the preparation method of the compound XV, the reaction time of the nucleophilic substitution reaction is 10 min-5.0 h;
or,
the preparation of the compound XV is carried out in the presence of an inert gas;
or,
the preparation method of the compound XV comprises the following steps: adding a mixture of the compound XIII and an organic solvent into a mixture of a base and an organic solvent at a temperature of −20° C. to −15° C., reacting for 10 min-20 min, then adding a mixture of the compound XIV and the organic solvent, reacting to obtain the compound XV.

14. The preparation method of the compound XV according to claim 11, comprising the following steps:
step 1: carrying out a ring-opening reaction on the polyene compound I under the presence of an aluminum salt catalyst and in an organic solvent to obtain the compound XIII;

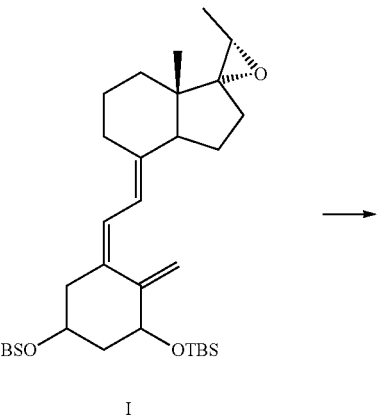

I

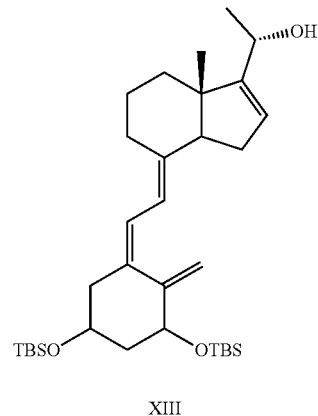

XIII step 2: carrying out a nucleophilic substitution reaction on the compound XIII with the compound XIV in the presence of a base and in an organic solvent to obtain the compound XV;

wherein, in the preparation method of the compound XIII, the organic solvent is one or more of benzene, toluene and xylene;

or, in the preparation method of the compound XIII, the volume-to-mass ratio of the organic solvent to the compound I is 5 mL/g-10 mL/g;

or, in the preparation method of the compound XIII, the molar ratio of the aluminum salt catalyst to the compound I is 0.1-0.3;

or, in the preparation method of the compound XIII, the temperature of the ring-opening reaction is 100° C. to 120° C.;

or, in the preparation method of the compound XIII, the reaction time of the ring-opening reaction is 1 h-3 h;

or, the preparation of the compound XIII is carried out in the presence of an inert gas selected from one or more of nitrogen, helium, argon, neon, krypton and xenon;

or, in the preparation method of the compound XV, the solvent is tetrahydrofuran;

or, in the preparation method of the compound XV, the solvent is N,N-dimethylformamide;

or, in the preparation method of the compound XV, the volume-to-mass ratio of the organic solvent to the compound XIII is 3 mL/g-10 mL/g;

or,

In the preparation method of the compound XV, the base is an inorganic base selected from one or more of sodium hydride, potassium hydride and potassium tert-butoxide;

or, in the preparation method of the compound XV, the base is an organic base selected from one or more of lithium hexamethyldisilazide, sodium hexamethyldisilazide and potassium hexamethyldisilazide;

or,

In the preparation method of the compound XV, the molar ratio of the base to the compound XIII is 2-3;

or, in the preparation method of the compound XV, the molar ratio of the compound XIV to the compound XIII is 1-1.5;

or, in the preparation method of the compound XV, the temperature of the nucleophilic substitution reaction is −15° C. to −5° C.;

or, in the preparation method of the compound XV, the reaction time of the nucleophilic substitution reaction is 30 min-60 min;

or, the preparation of the compound XV is carried out in the presence of an inert gas selected from one or more of nitrogen, helium, argon, neon, krypton and xenon.

15. The preparation method of the compound XIII according to claim 12, comprising carrying out a ring-opening reaction on the polyene compound I in the presence of an aluminum salt catalyst and in an organic solvent to obtain the compound XIII;

wherein,
in the preparation method of the compound XIII, the organic solvent is an aromatic hydrocarbon solvent;
or,
in the preparation method of the compound XIII, the volume-to-mass ratio of the organic solvent to the compound I is 2 mL/g-20 mL/g;
or,
in the preparation method of compound XIII, the aluminum salt catalyst is one or more of aluminum triisopropoxide, aluminum tri-sec-butoxide and aluminum tri-t-butoxide;
or,
in the preparation method of the compound XIII, the molar ratio of the aluminum salt catalyst to the compound I is 0.01-0.5;
or,
in the preparation method of the compound XIII, the temperature of the ring-opening reaction is 80° C. to 150° C.;
or,
in the preparation method of the compound XIII, the reaction time of the ring-opening reaction is 1 h-10 h;
or,
The preparation of the compound XIII is carried out in the presence of an inert gas.

16. The preparation method of the compound XIII according to claim 12, comprising carrying out a ring-opening reaction on the polyene compound I in the presence of an aluminum salt catalyst and in an organic solvent to obtain the compound XIII;

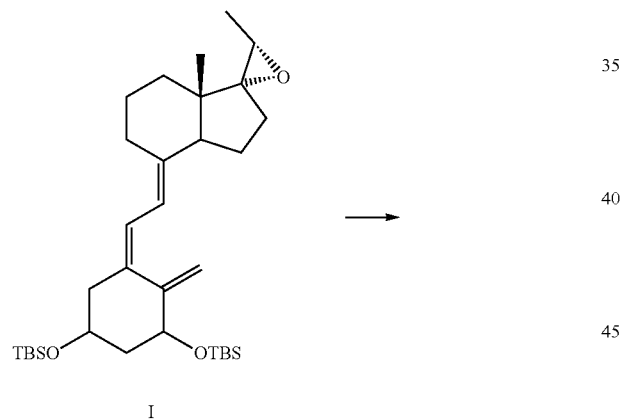

I

→

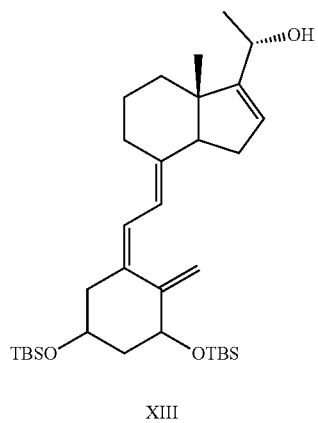

XIII wherein,
in the preparation method of the compound XIII, the organic solvent is one or more of benzene, toluene and xylene;
or,
in the preparation method of the compound XIII, the volume-to-mass ratio of the organic solvent to the compound I is 5 mL/g-10 mL/g;
or,
in the preparation method of the compound XIII, the molar ratio of the aluminum salt catalyst to the compound I is 0.1-0.3;
or,
in the preparation method of the compound XIII, the temperature of the ring-opening reaction is 100° C. to 120° C.;
or,
in the preparation method of the compound XIII, the reaction time of the ring-opening reaction is 1 h-3 h;
or,
the preparation of the compound XIII is carried out in the presence of an inert gas selected from one or more of nitrogen, helium, argon, neon, krypton and xenon.

* * * * *